US012102707B2

(12) United States Patent
Hakozaki et al.

(10) Patent No.: US 12,102,707 B2
(45) Date of Patent: *Oct. 1, 2024

(54) SKIN CARE COMPOSITION

(71) Applicant: The Procter & Gamble Company, Cincinnati, OH (US)

(72) Inventors: Tomohiro Hakozaki, Cincinnati, OH (US); Bin Fang Deyer, Loveland, OH (US); Leo Timothy Laughlin, II, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,625

(22) Filed: Aug. 28, 2023

(65) Prior Publication Data
US 2023/0404892 A1 Dec. 21, 2023

Related U.S. Application Data

(63) Continuation of application No. 16/455,988, filed on Jun. 28, 2019, now Pat. No. 11,786,451.

(51) Int. Cl.
| *A61K 8/67* | (2006.01) |
| *A61K 8/04* | (2006.01) |
| *A61K 8/29* | (2006.01) |
| *A61K 8/34* | (2006.01) |
| *A61K 8/368* | (2006.01) |
| *A61K 8/86* | (2006.01) |
| *A61K 8/891* | (2006.01) |
| *A61K 8/9783* | (2017.01) |
| *A61Q 19/02* | (2006.01) |

(52) U.S. Cl.
CPC ............ *A61K 8/675* (2013.01); *A61K 8/04* (2013.01); *A61K 8/29* (2013.01); *A61K 8/342* (2013.01); *A61K 8/347* (2013.01); *A61K 8/368* (2013.01); *A61K 8/86* (2013.01); *A61K 8/891* (2013.01); *A61K 8/9783* (2017.08); *A61Q 19/02* (2013.01)

(58) Field of Classification Search
CPC .......................... A61K 8/9783; A61Q 19/02
See application file for complete search history.

(56) References Cited

U.S. PATENT DOCUMENTS

| 6,294,181 | B1 | 9/2001 | Lezdey | |
| 6,296,859 | B1 | 10/2001 | Stoltz | |
| 7,338,671 | B2 | 3/2008 | Golz-Berner | |
| 8,173,184 | B2 | 5/2012 | Florence | |
| 8,673,372 | B2 | 3/2014 | Swanson et al. | |
| 9,629,793 | B2 | 4/2017 | Florence | |
| 10,034,830 | B2 | 7/2018 | Gruber | |
| 11,786,451 | B2* | 10/2023 | Hakozaki | A61K 8/347 |
| | | | | 424/62 |
| 2002/0012644 | A1 | 1/2002 | Chen | |
| 2002/0025303 | A1 | 2/2002 | Fructus | |
| 2005/0196373 | A1* | 9/2005 | Chen | A23L 21/25 |
| | | | | 424/728 |
| 2005/0255077 | A1 | 11/2005 | Golz-Berner et al. | |
| 2011/0097286 | A1 | 4/2011 | Swanson | |
| 2012/0156297 | A1 | 6/2012 | Loy | |
| 2015/0023893 | A1 | 1/2015 | Osbome et al. | |
| 2015/0352028 | A1 | 12/2015 | Tanner | |
| 2017/0154372 | A1 | 6/2017 | Balooch | |
| 2018/0344626 | A1 | 12/2018 | Leclere | |
| 2020/0405614 | A1 | 12/2020 | Hakozaki | |
| 2020/0405621 | A1 | 12/2020 | Hakozaki | |

FOREIGN PATENT DOCUMENTS

| AU | 2009282245 A1 | 2/2010 |
| AU | 2011242403 A1 | 12/2012 |
| CN | 101961298 A | 2/2011 |
| CN | 103284897 A | 9/2013 |
| CN | 103405377 A | 11/2013 |
| CN | 103655313 A | 3/2014 |
| CN | 103705429 A | 4/2014 |
| CN | 104027265 A | 9/2014 |
| CN | 103014106 B | 11/2014 |
| CN | 104224602 A | 12/2014 |
| CN | 104248572 A | 12/2014 |
| CN | 104367498 A | 2/2015 |
| CN | 104414897 A | 3/2015 |
| CN | 104414901 A | 3/2015 |
| CN | 104414918 A | 3/2015 |
| CN | 104414920 A | 3/2015 |

(Continued)

OTHER PUBLICATIONS

Abarike et al., "Exploring the Nutrient Potential of Nymphaea Alba (Water Lilly), for Use as Livestock Feed" UDS International Journal of Development, vol. 2 No. 1, Aug. 2015, pp. 1-11.
Abu Bakar et al., Jaundice (Hyperbilirubinemia) detection and prediction system using color card technique; 2017. IEEE 13th International Colloquium on Signal Processing & its Applications (CSPA 2017), Mar. 10-12, 2017, 06 Pages.
Alam et al., "Attenuation of melanogenesis by Nymphaea nouchali (Burm. f) flower extract through the regulation of CAMP/CREB/MAPKs/MITF and proteasomal degradation of tyrosinase", Scientific Reports, vol. 8., 2018, 14 pages.

(Continued)

*Primary Examiner* — Gina C Justice

(74) *Attorney, Agent, or Firm* — Alexandra S. Anoff

(57) ABSTRACT

Methods and compositions for improving the appearance of skin are provided. The methods and compositions are especially suited for inhibiting activation of PAR2 in skin by utilizing a synergistic combination of a water lily extract and vitamin $B_3$ compound. The method involves treating hyperpigmented skin by applying a skin care composition containing an effective amount of a combination of water lily extract and vitamin $B_3$ compound to a target portion of skin over the course of a treatment period.

13 Claims, No Drawings

(56) References Cited

FOREIGN PATENT DOCUMENTS

| | | |
|---|---|---|
| CN | 104414921 A | 3/2015 |
| CN | 104414955 A | 3/2015 |
| CN | 104415315 A | 3/2015 |
| CN | 104510640 A | 4/2015 |
| CN | 104510641 A | 4/2015 |
| CN | 104510643 A | 4/2015 |
| CN | 104510644 A | 4/2015 |
| CN | 104510647 A | 4/2015 |
| CN | 104510649 A | 4/2015 |
| CN | 104510650 A | 4/2015 |
| CN | 104510651 A | 4/2015 |
| CN | 104510653 A | 4/2015 |
| CN | 104513733 A | 4/2015 |
| CN | 104513737 A | 4/2015 |
| CN | 104513738 A | 4/2015 |
| CN | 104688600 A | 6/2015 |
| CN | 104940052 A | 9/2015 |
| CN | 104971024 A | 10/2015 |
| CN | 105287300 A | 2/2016 |
| CN | 105434277 A | 3/2016 |
| CN | 105434296 A | 3/2016 |
| CN | 105560158 A | 5/2016 |
| CN | 105748389 A | 7/2016 |
| CN | 105769736 A | 7/2016 |
| CN | 105902430 A | 8/2016 |
| CN | 106265256 A | 1/2017 |
| CN | 106265338 A | 1/2017 |
| CN | 106309196 A | 1/2017 |
| CN | 106389259 A | 2/2017 |
| CN | 106420421 A | 2/2017 |
| CN | 106420482 A | 2/2017 |
| CN | 106420579 A | 2/2017 |
| CN | 106511212 A | 3/2017 |
| CN | 106511239 A | 3/2017 |
| CN | 106551852 A | 4/2017 |
| CN | 106606436 A | 5/2017 |
| CN | 106619364 A | 5/2017 |
| CN | 106726919 A | 5/2017 |
| CN | 106727012 A | 5/2017 |
| CN | 106727038 A | 5/2017 |
| CN | 106727236 A | 5/2017 |
| CN | 106901191 A | 6/2017 |
| CN | 106902033 A | 6/2017 |
| CN | 106906084 A | 6/2017 |
| CN | 106963714 A | 7/2017 |
| CN | 107049852 A | 8/2017 |
| CN | 107260572 A | 10/2017 |
| CN | 107308062 A | 11/2017 |
| CN | 107320418 A | 11/2017 |
| CN | 107456415 A | 12/2017 |
| CN | 107496191 A | 12/2017 |
| CN | 107519034 A | 12/2017 |
| CN | 107595756 A | 1/2018 |
| CN | 107616927 A | 1/2018 |
| CN | 107616953 A | 1/2018 |
| CN | 107648171 A | 2/2018 |
| CN | 107714618 A | 2/2018 |
| CN | 107789281 A | 3/2018 |
| CN | 107789306 A | 3/2018 |
| CN | 107811959 A | 3/2018 |
| CN | 107823005 A | 3/2018 |
| CN | 107854362 A | 3/2018 |
| CN | 107854383 A | 3/2018 |
| CN | 107998061 A | 5/2018 |
| CN | 108186482 A | 6/2018 |
| CN | 108210423 A | 6/2018 |
| CN | 108210440 A | 6/2018 |
| CN | 108379162 A | 8/2018 |
| CN | 108542839 A | 9/2018 |
| CN | 109288781 A | 2/2019 |
| DE | 10139612 C1 | 5/2003 |
| FR | 2871380 B1 | 9/2006 |
| FR | 2914185 A1 | 10/2008 |
| FR | 2921830 A1 | 4/2009 |
| FR | 3026946 A1 | 4/2016 |
| FR | 3058057 A1 | 5/2018 |
| JP | 2008037812 A | 2/2008 |
| JP | 2014172906 A | 9/2014 |
| JP | 2015510897 A | 4/2015 |
| KR | 715485 B1 | 4/2007 |
| KR | 1181541 B1 | 9/2012 |
| KR | 1277162 B1 | 6/2013 |
| KR | 20140110376 A | 9/2014 |
| KR | 1595530 B1 | 2/2016 |
| KR | 2016012631 A | 2/2016 |
| KR | 1691495 B1 | 12/2016 |
| KR | 1744579 B1 | 6/2017 |
| KR | 1763736 B1 | 7/2017 |
| KR | 1799313 B1 | 11/2017 |
| KR | 2017136958 A | 12/2017 |
| KR | 101985884 B1 | 9/2019 |
| WO | 0064279 A1 | 11/2000 |
| WO | 2010033494 A2 | 3/2010 |
| WO | 2011130788 A1 | 10/2011 |
| WO | 2018144093 A2 | 8/2018 |

OTHER PUBLICATIONS

All Office Actions; U.S. Appl. No. 16/455,966, filed Jun. 28, 2019.
All Office Actions; U.S. Appl. No. 16/455,988, filed Jun. 28, 2019; See Pair.
Bakr, Riham O., "Nymphaea alba and Liver Protection", Dietary Interventions in Liver Disease, Chapter 11, 2009, pp. 135-143.
Bowe et al. Journal of drugs in dermatology 13, 9, (2014), Year 2014, pp. 1021-1024.
Cosmetic Ingredient Review. Liebert, M. A. Int. J. Toxicol 2 (1983), pp. 17-34, Year: 1983.
Dailymed Cellpium. Niacinamide Cream, FDA report, Mar. 2016; retrieved from URL:https://fda.report/DailyMed/e2Oeb6Oc-3bb8-4cd7-a916-7a886d9a32e2 on Mar. 17, 2023) (Year: 2016), pp. 04.
Devi et al., "Nymphaea rubra Roxb. ex Andrews cultivated as an ornamental, food and vegetable in the North Eastern region of India", Genetic Resources and Crop Evolution, vol. 62(2), 2015, pp. 315-320.
EWG's Skin Deep_A.H.C the Pure Real Eye Cream for Face Rating, Jul. 2017, URL Link—https://www.ewg.org/skindeep/products/741269-AHC_The_Pure_Real_Eye_Cream_For_Face/, year 2020, 15 pages.
Gayani, Pathirage Anusha, "Anti-oxidant and anti-tyrosinase natural products of Nyphaea stellata", Dissertation, 2009, 3 pages.
Hongrong et al., "Study on inhibition of ethanol extract from nymphaca hybrid on the activity of tyrosinase", Detergents & Cosmetics, 2009, 2 pages.
Huang, Tingyu, "Studies on Chinese herbal medicine used in whitening cosmetics", URL: https://hdl.handle.net/11296/k7gpkr, year 2010, 2 pages.
15580 PCT Search Report and Written Opinion for PCT/US2020/070184, dated Oct. 20, 2020, 13 pages.
John Woodruff, "Skin Lightening—Light and Smooth and Even", retrieved from http://www.cosmeticsbusiness.com/story.asp?storycode=2871, Aug. 21, 2008, 5 pages.
Kim et al., "Inhibitory effects of natural plants of Jeju Island on elastase and MMP-1 expression", J Cosmet Sci., vol. 58, 2007, pp. 19-33.
MacPhillamy, H.B., and From Plants Drugs, "Plant Science Bulletin." A Publication of the Botanical Society of America, Inc9.2 (1963), Year 1963, , pp. 15.
Malinowska, Paulina, "Skin-whitening Cosmetics and Cosmeceuticals Available on Polish Cosmetics Market", Commodity Quality Problems, 2011, pp. 91-100.
Mintel, "Brassica Lightening Facial Serum", retrieved from www.gnpd.com, Database Accession No. 6368359 Abstract, XP055734162, Mar. 1, 2019, 4 pages.
Paharia, A. K., and A. Pandurangan. "Evaluation of hepatoprotective activity of ethanolic extract of Nymphaea alba Linn flower inexperimental rats." Int J Biomed Res 4.7 (2013), Year: 2013, , pp. 349-35.

(56) References Cited

OTHER PUBLICATIONS

Parimala et al., Evaluation of Antidiabetic Potential of Nymphaea nouchali Burm. f. Seeds in STZ-Induced Diabetic Rats, International Journal of Pharmacy and Pharmaceutical Sciences, vol. 6, Issue 4, 2014, pp. 536-541.

Parimala et al., Phytochemical analysis and in vitro antioxidant activity of hydroalcoholic seed extract of Nymphaea nouchali Burm. f., Asian Pacific Journal of Tropical Biomedicine 2013; 3(11): 887-895.

Park et al., "Protection on Skin Aging Mediated byAntiapoptosis Effects of the Water Lily (*Nymphaea tetragona georgi*) via Reactive Oxygen Species Scavenging in Human Epidermal Keratinocytes", Pharmacology, vol. 97, 2016, pp. 282-293.

Park, K., Role of Micronutrients in Skin Health and Function, Biomolecules & Therapeutics 23(3), 2015, pp. 207-217.

Puri, Munish, Deepika Sharma, and Colin J. Barrow. "Enzyme-assisted extraction of bioactives from plants." Trends inbiotechnology 30.1 (2012), Year 2012, pp. 37-44.

Rao et al. "Optimization of extraction conditions of Guangchang white lotus seed protein by response surface methodology andantioxidant activities of its enzymatic hydrolysates", Food Science, 2015-14, 3 pages.

Rao, Yazhen, "Antioxidant, anti-inflammatory, antimelanogenio and aoptotic effects of Nymphaea mexicana Zucc. Flower", Dissertation, 2009, 7 pages.

Raskin, Ilya, and Christophe Ripoll. "Can an apple a day keep the doctor away?" Current pharmaceutical design 10.27 (2004), Year 2004, pp. 3419-3429.

Revilla, et al. "Study of the extraction of proanthocyanidins from grape seeds." Food Chemistry 61.1-2 (1998), pp. 201-206, Year 1998.

Sable et al., "A review on Lotus: use in herbal cosmetics", Res. J. Topical and Cosmetic Sci., vol. 4(1), 2013, pp. 81-83.

Seiberg et al., The Protease-Activated Receptor 2 Regulates Pigmentation via Keratinocyte-Melanocyte Interactions, Experimental Cell Research 254, 2000, pp. 25-32.

Stoltz, C., "A new soothing active ingredient adapted to sun damaged skin", SOFW—Journal, vol. 125, 1999, pp. 16, 18-20.

\* cited by examiner

SKIN CARE COMPOSITION

FIELD

The present invention is directed generally to compositions and methods of inhibiting par-2 activation in skin. More specifically, the present invention is directed to compositions and methods that utilize a combination of water lily extract and a vitamin $B_3$ compound to synergistically inhibit par-2 activation.

BACKGROUND

Melanin is fundamental compound in skin pigmentation. Melanin is produced by a complex series of biochemical reactions within a melanocyte involving, at a basic level, the enzyme tyrosinase and L-tyrosine as a substrate. Tyrosinase catalyzes the conversion of L-tyrosine to DOPA (L-3,4-dihydroxyphenyialanine) and of DOPA to dopaquinone. Dopaquinone undergoes further conversion to form melanin, which aggregates in organelles known as melanosomes. Melanosomes are then transferred to keratinocytes along the slender filaments of a melanocyte known as dendrites.

There are approximately 1500 gene products expressed in melanocytes, with 600 of them being expressed at any given time and 100 of them believed to be unique to the melanosome. In addition, there are many regulatory elements involved in signaling, transport of melanosomes within the melanocyte, and transfer of melanosomes to the keratinocytes. One mechanism in the melanin production cycle is the transfer of melanosomes from the melanocytes to the keratinocytes by way of phagocytosis. Research has found that the protease-activated receptor-2 gene (PAR2) expressed on keratinocytes is involved in melanosome transfer and therefore may regulate pigmentation. See, Seiberg, M., et al., The Protease-Activated Receptor 2 Regulates Pigmentation via. Keratinocyte-Melanocyte Interactions, Experimental Cell Research 254, 25-32 (2000). Activation of PAR2 with trypsin (or a trypsin-like protease) or protease-activated receptor-2 activating peptide (SLIGRL) induces pigmentation, which in some cases may manifest as a hyperpigmented spot or uneven skin tone. Therefore, compounds that inhibit trypsin activation of PAR2 are believed to disrupt or reduce the phagocytosis of the melanocytes by the keratinocytes. Compounds that inhibit the PAR2 activation may help regulate hyperpigmentation and melanin overproduction.

Conditions associated with overproduction of melanin are referred to as "hyperpigmentation" and are characterized by the development of sharply demarcated blotchy, brown spots usually in a symmetric distribution over the cheeks, forehead, and sometimes on the upper lip and neck. Active ingredients marketed for improving the appearance of hyperpigmented skin are known. For example, the use of N-acyl amino acid compounds (e.g., N-acyl phenylalanine and N-acyl tyrosine) and vitamin $B_3$ compounds have been shown to be beneficial in the regulation of melanin production in vitro. See Millikin, C. L., et al. (2008, February). However, there is a continuing need for new actives that are effective at regulating hyperpigmentation.

Accordingly, it would be desirable to provide an improved method of inhibiting PAR2 activation in skin to treat a hyperpigmented skin condition.

SUMMARY

A method of treating hyperpigmented skin, comprising: a) identifying a target portion of skin on a person where treatment is desired; and applying a composition comprising an effective amount of water lily extract and vitamin B3 compound to the target portion of skin during a treatment period, wherein the water lily extract and vitamin B3 compound are present at a volume/weight ratio of water lily extract to niacinamide of 1:4 to 5:1.

DETAILED DESCRIPTION

There is a long felt need for cosmetic skin care actives that improve the appearance of hyperpigmented skin and/or inhibit or even prevent skin hyperpigmentation. Vitamin $B_3$ compounds such as niacinamide are known for use in treating hyperpigmentation conditions by suppressing melanin transfer from melanocytes to keratinocytes. Water lily extract (INCI: *Nymphaea alba* Flower Extract) is known for use in treating irritated skin and promoting wound healing. However, water lily extract was not known for treating hyperpigmented skin or for inhibiting PAR2 activation. It has now been discovered that water lily inhibits PAR2 activation and, surprisingly, when water lily extract and a vitamin B3 compound are combined at certain ratios, they synergistically inhibit PAR2 activation.

Reference within the specification to "embodiment(s)" or the like means that a particular material, feature, structure and/or characteristic described in connection with the embodiment is included in at least one embodiment, optionally a number of embodiments, but it does not mean that all embodiments incorporate the material, feature, structure, and/or characteristic described. Furthermore, materials, features, structures and/or characteristics may be combined in any suitable manner across different embodiments, and materials, features, structures and/or characteristics may be omitted or substituted from what is described. Thus, embodiments and aspects described herein may comprise or be combinable with elements or components of other embodiments and/or aspects despite not being expressly exemplified in combination, unless otherwise stated or an incompatibility is stated.

In all embodiments, all ingredient percentages are based on the weight of the cosmetic composition, unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at approximately 25° C. and at ambient conditions, where "ambient conditions" means conditions under about 1 atmosphere of pressure and at about 50% relative humidity. All numeric ranges are inclusive of narrower ranges; delineated upper and lower range limits are interchangeable to create further ranges not explicitly delineated.

The compositions of the present invention can comprise, consist essentially of, or consist of, the essential components as well as optional ingredients described herein. As used herein, "consisting essentially of" means that the composition or component may include additional ingredients, but only if the additional ingredients do not materially alter the basic and novel characteristics of the claimed compositions or methods. As used in the description and the appended claims, the singular forms "a," "an," and "the" are intended to include the plural forms as well, unless the context clearly indicates otherwise.

The genes and proteins disclosed herein correspond to their respective known sequences as of Jun. 24, 2019.

Definitions

"About" modifies a particular value by referring to a range equal to plus or minus twenty percent (+/−20%) or less (e.g., less than 15%, 10%, or even less than 5%) of the stated value.

"Apply" or "application", as used in reference to a composition, means to apply or spread the compositions of the present invention onto a human skin surface such as the epidermis.

"Cosmetic agent" means any substance, as well any component thereof, intended to be rubbed, poured, sprinkled, sprayed, introduced into, or otherwise applied to a mammalian body or any part thereof to provide a cosmetic effect. Cosmetic agents may include substances that are Generally Recognized as Safe (GRAS) by the US Food and Drug Administration, food additives, and materials used in non-cosmetic consumer products including over-the-counter medications.

"Cosmetic composition" means a composition comprising a cosmetic agent such as the water lily extract described herein. Examples of cosmetic compositions include color cosmetics (e.g., foundations, lipsticks, concealers, and mascaras), skin care compositions (e.g., moisturizers and sunscreens), personal care compositions (e.g., rinse-off and leave on body washes and soaps), hair care compositions (e.g., shampoos and conditioners).

"Effective amount" means an amount of a compound or composition sufficient to significantly induce a positive benefit to keratinous tissue over the course of a treatment period. The positive benefit may be a health, appearance, and/or feel benefit, including, independently or in combination, the benefits disclosed herein. In a specific example, effective amount means an amount of a water lily extract and a vitamin $B_3$ compound, in combination, sufficient to provide a desired benefit (e.g., synergistic reduction in PAR2 activation or improvement in the appearance of a hyperpigmented spot).

"Enzymatic hydrolysate" mean an extract obtained (e.g., from *Nymphaea alba*) using a method comprising at least one enzymatic hydrolysis step.

"Hydrolysate" means an extract obtained (e.g., from *Nymphaea alba*) by using a method comprising at least one enzymatic or chemical hydrolysis step.

"Hyperpigmented spot" means a defined area of skin wherein the pigmentation is greater than that of an adjacent area of skin due to localized and chronic or systemic overproduction of melanin. Hyperpigmented spots are typically between 2 mm and 10 mm in diameter, but smaller or larger spots are possible. Examples of commonly known hyperpigmented spots are age spots, sun spots, solar lentigos, hypo-melanotic lesions, freckles, and melasma spots.

"Improve the appearance of" means providing a measurable, desirable change or benefit in male and/or female skin tone appearance, which may be quantified, for example, by a decrease in b* value of skin or a change in the size and/or appearance of a hyperpigmented spot. Exemplary methods for determining improvements in appearance are described in more detail below.

"Juice" refers to the liquid expelled from water lily plant material as a result of pressing or other mechanical processing. Juice can contain solid particles, semi-solid particles, and/or droplets of water-immiscible liquids of a variety of sizes (collectively referred to as "water lily particles") in an aqueous serum.

"L*a*b*" refers to the commonly recognized color space specified by the International Commission on Illumination ("CIE"). The three coordinates represent (i) the lightness of the color (i.e., L*=0 yields black and L*=100 indicates diffuse white), (ii) the position of the color between magenta and green (i.e., negative a* values indicate green while positive a* values indicate magenta) and (iii) the position of the color between yellow and blue (i.e., negative b* values indicate blue and positive b* values indicate yellow).

"Safe and effective amount" means an effective amount of an ingredient that is low enough to avoid serious side effects (within the scope of sound medical judgment).

"Skin care" means regulating and/or improving a skin condition. Some nonlimiting examples include improving skin appearance and/or feel by providing a smoother, more even appearance and/or feel; increasing the thickness of one or more layers of the skin; improving the elasticity or resiliency of the skin; improving the firmness of the skin; and reducing the oily, shiny, and/or dull appearance of skin, improving the hydration status or moisturization of the skin, improving the appearance of fine lines and/or wrinkles, improving skin exfoliation or desquamation, plumping the skin, improving skin barrier properties, improve skin tone, reducing the appearance of redness or skin blotches, and/or improving the brightness, radiancy, or translucency of skin.

"Skin care active" means a compound or combination of compounds that, when applied to skin, provide an acute and/or chronic benefit to skin or a type of cell commonly found therein. Skin care actives may regulate and/or improve skin or its associated cells (e.g., improve skin elasticity, hydration, skin barrier function, and/or cell metabolism).

"Skin care composition" means a composition that includes a skin care active and regulates and/or improves skin condition.

"Skin tone" means the overall appearance of basal skin color or color evenness. Skin tone is typically characterized over a larger area of the skin, which is generally more than 100 $mm^2$, up to and including the entirety of the facial skin or other bodily skin surface (e.g., arms, legs, back, hands, neck, chest and abdomen), as opposed to a localized skin pigmentation feature such as a hyperpigmented spot. Skin tone can be measured by image analysis. One measure of skin tone is lightness, which can be measured by the L* coordinate in the L*a*b* color space (International Commission on Illumination). Chromophore mapping such as melanin mapping and melanin concentration may also be used as an indicator of skin tone. Mean melanin may be calculated from the chromophore map data. Additionally, skin tone can be correlated to melanin evenness (e.g., standard deviation) which also may be calculated from the chromophore map data.

"Synergy" and variations thereof mean that the effect provided by a combination of two or more materials (e.g., a vitamin $B_3$ compound and water lily extract) is more than the additive effect expected for these materials. For example, synergy is demonstrated when PAR2 activation is inhibited by a combination of niacinamide and water lily extract is more than their calculated additive effect.

"Treatment period," as used herein, means the length of time and/or frequency that a material or composition is applied to a target skin surface.

Composition

The compositions herein contain an effective amount of a combination of water lily extract and vitamin $B_3$ compound disposed in a dermatologically acceptable carrier and are intended for topical application to human skin. The amount of water lily extract and vitamin $B_3$ compound should be sufficient to demonstrate an in vitro PAR2 inhibition benefit and/or improve the appearance of hyperpigmented skin after a suitable course of treatment (e.g., 2, 4 or 8 weeks). It has been surprisingly discovered that ratios (volume/weight) of water lily extract to vitamin $B_3$ compound ranging from 1:4 to 5:1 (e.g., 1:2 to 2.5:1) can synergistically inhibit PAR2 activation, while ratios outside of this range do not. The present skin care compositions may optionally include one or more additional skin actives or other ingredients of the type commonly included in topical skin care compositions. The skin care compositions herein may be made using conventional methods of combining skin care ingredients.

The skin care compositions herein may be cosmetic compositions, pharmaceutical compositions, or cosmeceutical compositions, and may be provided in various product forms, including, but not limited to, solutions, suspensions, lotions, creams, gels, toners, sticks, sprays, aerosols, ointments, cleansing liquid washes and solid bars, pastes, foams, mousses, shaving creams, wipes, strips, patches, electrically-powered patches, hydrogels, film-forming products, facial and skin masks (with and without insoluble sheet), make-up such as foundations, eye liners, and eye shadows, and the like. In some instances, the composition form may follow from the particular dermatologically acceptable carrier chosen. For example, the composition (and carrier) may be provided in the form of an emulsion (e.g., water-in-oil, oil-in-water, or water-in-oil-in water) or an aqueous dispersion.

Water Lily Extract

The compositions herein include an effective amount of water lily extract obtained from a plant in the genus *Nymphaea*. The water lily extract may be provided as a liquid (e.g., an aqueous solution containing water lily plant material) or as a solid (e.g., a powder formed by drying the liquid water lily extract and/or a maltodextrin carrier thereof). The water lily extract may be mixed with a suitable carrier prior to incorporation into the cosmetic composition. For example, powdered water lily extract may be mixed with a maltodextrin carrier (e.g., at a ratio of 1:9) or an aqueous carrier (e.g., water and/or a water soluble/miscible material). The amount of extract that is effective can differ from one particular source of extract to another (e.g., supplier), and can be determined by the skilled artisan, for example, by measuring the level of PAR2 activation inhibition according to the PAR2 Inhibition Assay described in more detail below. As with any extract, the concentration of active components and/or level of activity of a particular extract will depend on factors such as the final dilution volume of the extract product, the particular extraction method employed, the natural range of variation among individual plants, and other common factors known to those skilled in the art.

The water lily extract of the present invention may be Obtained from a suitable species of water lily and/or portion of the water lily plant (e.g., flower, root, leaf, stem, seed, juice, and combinations of these), as long as the extract provides the desired PAR2 activation inhibition. Examples of water lily species that may be suitable for use herein include *Nymphaea alba, Nymphaea gigantea, Nymphaea tetragona, Nymphaea lotus, Nymphaea caerulea, Nymphaea pubescens, Nymphaea amazonum, Nytriphaea ampla, Nymphaea blanda, Nymphaea calliantha, Nymphaea candida, Nymphaea capensis, Nymphaea colorata, Nymphaea conardii, Nymphaea elegans, Nymphaea fennica, Nymphaea flavovirens, Nymphaea gardneriana, Nymphaea glandulifera, Nymphaea heudelotii, Nymphaea jamesoniana, Nymphaea leibergii, Nymphaea macrosperma, Nymphaea mexicana, Nymphaea micrantha, Nymphaea nouchali, Nymphaea odorata, Nymphaea rubra, Nymphaea rudgeana, Nymphaea stuhlmannii, Nymphaea sulfurea, Nymphaea thermarum*, and *Nymphaea violacea*. Extracts obtained from the flower of *Nymphaea alba* may be particularly suitable for use in the compositions herein. *Nymphaea alba* includes *Castalia alba* (L.) Greene, *Castalia minoriflora* Simonk, *Castalia speciosa* Salisb, *Nymphaea occidentalis* Moss or *Nymphaea minoriflora* (Simonk.) Wissjul, but does not include species of *Lotus* or *Nelumbo nucifera*.

The water lily extract may be in the form of a yellow, odorless, aqueous solution with a dry matter content of between about 10 and 55 g/L (e.g., between 15 and 45 g/L between 20 and 40 g/L, or even between 24 and 35 g/L). The active ingredient obtained from water lily extract may contain a carbohydrate, protein or mineral, hydrolysates of these and combinations thereof. In some instances, the hydrolysate may include an enzymatic hydrolysate, obtained by conducting one or more enzymatic hydrolyses on the water lily extract or components thereof (e.g., carbohydrate or protein). When two more enzymatic hydrolyses are conducted, different types of enzymes may be used (e.g., a carbohydrase and a protease, two different carbohydrases, or two different proteases). The water lily extract may have a carbohydrate fraction of between 20% and 70% (e.g., 23% to 62% or 25% to 55%) by weight, based on the weight of the dry matter. The carbohydrate content can be determined by the DUBOIS method (Dubois M et al., Analytical Chemistry, 28, 3, 350-356, 1956) and expressed as a percentage of the total dry matter content of the water lily extract. In some instances, the water lily extract may have a mineral fraction of between 20% and 60% (e.g., 25% to 50% or even 30% to 45%) by weight, based on the weight of the dry matter. Mineral fraction can by determined by weighing the crude ash residue resulting from incineration of the samples of the active ingredient at 550° C. in an electric muffle furnace.

It may be desirable to minimize or eliminate the amount of peptides/proteins and/or polyphenols present in the water lily extract, which can reduce the risk of an allergic response or other adverse reaction from a user. Accordingly, the water lily extracts herein may have a peptide fraction of less than 20% (e.g., less than 15%, 10%, or even less than 5%) by weight, based on the weight of the dry matter, and may be free of or substantially free of polyphenol compounds (i.e., less than 3%, 1%, 0.5%, or even less than 0.2% by weight, based on the weight of the dry matter). The protein fraction of the water lily extract can be determined by the LOWRY method (Lowry et al., Protein measurement with the Folin reagent, J. Biol. Chem., 193, 265, 1951). In some instances, it may also be desirable to determine the size of the peptide compounds that are present, e.g., via FPLC type chromatography. The content of polyphenolic compounds can be determined according to the method provided in more detail below. The peptide/protein and/or polyphenol levels in the water lily extract may be provided as part of the initial process to obtain the water lily extract from the plant material or by subjecting the water lily extract to further processing.

In some instances, the water lily extract may be mixed with other suitable materials (e.g., water, thickeners, humectants, solvents, preservatives, and/or solubilizers) prior to incorporation into a composition. For example, the water lily extract may be mixed with water or another suitable carrier e.g., a polyhydric alcohol such as glycerin) to provide a mixture containing 0.001% to 50% (e.g., 0.01% to 40%, 0.1% to 20%, 0.5% to 10%, or even 1% to 5%) water lily extract. The water lily extract and/or water lily mixture may be included in a composition at an amount of 0.00001% to 15%, 0.0001% to 10%, 0.01% to 15%, 0.025% to 10%, 0.05% to 10%, 0.05% to 5%, or even 0.1% to 5%, by weight.

Vitamin $B_3$ Compound

As used herein, "vitamin $B_3$ compound" means a compound having the formula:

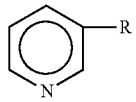

wherein R is —$CONH_2$ (i.e., niacinamide), —COOH (i.e., nicotinic acid) or —$CH_2OH$ (i.e., nicotinyl alcohol); derivatives thereof; and salts of any of the foregoing. The vitamin $B_3$ compound may be present at an amount of from 0.00005% to 15%, from 0.0001% to 10%, from 0.001% to 15%, from 0.025% to 10 from 0.05% to 10%, from 0.05% to 5%, or even from 0.1% to 5%, by weight of the total composition. A particular suitable vitamin $B_3$ compound is niacinamide.

Dermatologically Acceptable Carrier

The skin care compositions herein include a dermatologically acceptable carrier (which may be referred to as a "carrier"). The phrase "dermatologically acceptable carrier" means that the carrier is suitable for topical application to the keratinous tissue, has good aesthetic properties, is compatible with the actives in the composition, and will not cause any unreasonable safety or toxicity concerns. In one embodiment, the carrier is present at a level of from about 50% to about 99%, about 60% to about 98%, about 70% to about 98%, or, alternatively, from about 80% to about 95%, by weight.

The carrier can be in a wide variety of forms. In some instances, the solubility or dispersibility of the components (e.g., extracts, sunscreen active, additional components) may dictate the form and character of the carrier. Non-limiting examples include simple solutions (e.g., aqueous or anhydrous), dispersions, emulsions, and solid forms (e.g., gels, sticks, flowable solids, or amorphous materials). In some instances, the dermatologically acceptable carrier is in the form of an emulsion. The emulsion may have a continuous aqueous phase (e.g., an oil-in-water or water-in-oil-in-water emulsion) or a continuous oil phase (e.g., water-in-oil or oil-in-water-in-oil emulsion). The oil phase of the present invention may comprise silicone oils, non-silicone oils such as hydrocarbon oils, esters, ethers, and mixtures thereof. The aqueous phase typically comprises water and water-soluble ingredients (e.g., water-soluble moisturizing agents, conditioning agents, anti-microbials, humectants and/or other skin care actives). However, in some instances, the aqueous phase may comprise components other than water, including but not limited to water-soluble moisturizing agents, conditioning agents, anti-microbials, humectants and/or other water-soluble skin care actives. In some instances, the non-water component of the composition comprises a humectant such as glycerin and/or other polyol(s).

In some instances, the compositions herein are in the form of an oil-in-water ("O/W") emulsion that provides a sensorial feel that is light and non-greasy. Suitable O/W emulsions herein may include a continuous aqueous phase of more than 50% by weight of the composition, and the remainder being the dispersed oil phase. The aqueous phase may include 1% to 99% water, based on the weight of the aqueous phase, along with any water soluble and/or water miscible ingredients. In these instances, the dispersed oil phase will typically be present at less than 30% by weight of composition (e.g., 1% to 20%, 2% to 15%, 3% to 12%, 4% to 10%, or even 5% to 8%) to help avoid some of the undesirable feel effects of oily compositions. The oil phase may include one or more volatile and/or non-volatile oils (e.g., botanical oils, silicone oils, and/or hydrocarbon oils). Some nonlimiting examples of oils that may be suitable for use in the present compositions are disclosed in U.S. Pat. No. 9,446,265 and U.S. Publication No. 2015/0196464.

The carrier may contain one or more dermatologically acceptable, hydrophilic diluents. As used herein, "diluent" includes materials in which the water lily extract can be dispersed, dissolved, or otherwise incorporated. Hydrophilic diluents include water, organic hydrophilic diluents such as lower monovalent alcohols (e.g., $C_1$-$C_4$) and low molecular weight glycols and polyols, including propylene glycol, polyethylene glycol (e.g., molecular weight of 200 to 600 g/mole), polypropylene glycol (e.g., molecular weight of 425 to 2025 g/mole), glycerol, butylene glycol, 1,2,4-butanetriol, sorbitol esters, 1,2,6-hexanetriol, ethanol, isopropanol, sorbitol esters, butanediol, ether propanol, ethoxylated ethers, propoxylated ethers and combinations thereof.

Other Optional Ingredients.

The present composition may optionally include one or more additional ingredients commonly used in cosmetic compositions (e.g., colorants, skin care actives, anti-inflammatory agents, sunscreen agents, emulsifiers, buffers, rheology modifiers, combinations of these and the like), provided that the additional ingredients do not undesirably alter the skin health or appearance benefits provided by the present compositions. The additional ingredients, when incorporated into the composition, should be suitable for use in contact with human skin tissue without undue toxicity, incompatibility, instability, allergic response, and the like. Some nonlimiting examples of additional actives include vitamins, minerals, peptides and peptide derivatives, sugar amines, sunscreens, oil control agents, particulates, flavonoid compounds, hair growth regulators, anti-oxidants and/or anti-oxidant precursors, preservatives, protease inhibitors, tyrosinase inhibitors, anti-inflammatory agents, moisturizing agents, exfoliating agents, skin lightening agents, sunless tanning agents, lubricants, anti-acne actives, anti-cellulite actives, chelating agents, anti-wrinkle actives, anti-atrophy actives, phytosterols and/or plant hormones, N-acyl amino acid compounds, antimicrobials, and antifungals. Other non-limiting examples of additional ingredients and/or skin care actives that may be suitable for use herein are described in U.S. Publication Nos. 2002/0022040; 2003/0049212; 2004/0175347; 2006/0275237; 2007/0196344; 2008/0181956; 2008/0206373; 2010/00092408; 2008/0206373; 2010/0239510; 2010/0189669; 2010/0272667; 2011/0262025; 2011/0097286; US2012/0197016; 2012/0128683; 2012/0148515; 2012/0156146; and 2013/0022557; and U.S. Pat. Nos. 5,939,082; 5,872,112; 6,492,326; 6,696,049; 6,524,598; 5,972,359; and 6,174,533.

Conditioning Agents

The compositions herein may include 0.1% to 50% by weight of a conditioning agent (e.g., 0.5% to 30%, 1% to 20%, or even 2% to 15%). Adding a conditioning agent can help provide the composition with desirable feel properties (e.g., a silky, lubricious feel upon application). Some non-limiting examples of conditioning agents include, hydrocarbon oils and waxes, silicones, fatty acid derivatives, cholesterol, cholesterol derivatives, diglycerides, triglycerides, vegetable oils, vegetable oil derivatives, acetoglyceride esters, alkyl esters, alkenyl esters, lanolin, wax esters, beeswax derivatives, sterols and phospholipids, salts, isomers and derivatives thereof, and combinations thereof. Particularly suitable examples of conditioning agents include volatile or non-volatile silicone fluids such as dimethicone copolyol, dimethylpolysiloxane, diethylpolysiloxane, mixed C1-30 alkyl polysiloxanes, phenyl dimethicone, dimethiconol, dimethicone, dimethiconol, silicone crosspolymers, and combinations thereof. Dimethicone may be especially suitable, since some consumers associate the feel properties provided by certain dimethicone fluids with good moisturization. Other examples of silicone fluids that may be suitable for use as conditioning agents are described in U.S. Pat. No. 5,011,681.

Rheology Modifiers

The compositions herein may include 0.1% to 5% of a rheology modifier (e.g., thickening agent) to provide the composition with suitable rheological and skin feels properties. Some non-limiting examples of thickening agents include crosslinked polyacrylate polymers, polyacrylamide polymers, polysaccharides, gums and mixtures thereof. In a particularly suitable example, the composition may include a superabsorbent polymer thickening agent such as sodium polyacrylate, starch grafted sodium polyacrylate, or a combination of these. Some non-limiting examples of superabsorbent polymer thickeners are described in, for example, U.S. Pat. No. 9,795,552.

Some consumers find compositions that use silicone fluids as conditioning agents to be undesirably greasy or heavy feeling. Thus, it may be desirable to provide a composition that is free of or substantially free of silicone fluid. It may also be desirable to tailor a superabsorbent polymer thickener to provide the composition with a light, airy feel, for example, by adjusting the amount of water in the composition, the water:oil ratio (e.g., 12:1 to 1:1), and/or the ratio of water to thickener or oil to thickener.

Emulsifiers

When the dermatologically acceptable carrier is in the form of an emulsion, it may be desirable to include an emulsifier to provide a stable composition (e.g., does not phase separate). When included, the emulsifier may be present at an amount of 0.1% to 10% (e.g., 1% to 5%, or 2%-4%). Emulsifiers may be nonionic, anionic or cationic. Some non-limiting examples of emulsifiers that may be suitable for use herein are disclosed in U.S. Pat. Nos. 3,755,560; 4,421,769; and McCutcheon's Detergents and Emulsifiers, North American Edition, pages 317-32.4 (1986).

When including optional ingredients in the compositions herein, it may be desirable to select ingredients that do not form complexes or otherwise undesirably interact with other ingredients in the composition at low pH, especially pH sensitive ingredients like niacinamide, salicylates and peptides (e.g., palmitoyl-lysine-threonine (pal-KT) or palmitoyl-lysine-threonine-threonine-lysine-serine (pal-KTTKS). In some instances, it may be desirable to select skin care actives that function via different biological pathways so that the actives do not interfere with one another, which could reduce the efficacy of both agents. When present, the optional ingredients may be included at amounts of from 0.0001% to 50%; from 0.001% to 20%; or even from 0.01% to 10% (e.g., 50%, 40%, 30%, 20%, 10%, 5%, 4%, 3%, 2%, 1%, 0.5% or 0.1%), by weight of the composition.

Method of Use

The present method includes identifying a target portion of skin on a person in need of treatment and applying a composition comprising an effective amount of water lily extract and vitamin $B_3$ compound, and optionally one or more additional skin care agents, to the target portion of skin. The target portion of skin may be on a facial skin surface such as the forehead, perioral, chin, periorbital, nose, and/or cheek) or another part of the body (e.g., hands, arms, legs, back, chest). The person in need of treatment may be one who exhibits a hyperpigmented skin condition. In some instances, a target portion of skin may not exhibit a hyperpigmentation condition, but a user may still wish to treat the target portion of skin as a preventative measure if it is one that is prone to developing hyperpigmentation (e.g., sun exposed skin such as facial skin and arm skin). In this way, the present methods and compositions may be used prophylactically.

The composition may be applied to a target portion of skin and, if desired, to the surrounding skin at least once a day, twice a day, or on a more frequent daily basis, during a treatment period. When applied twice daily, the first and second applications are separated by at least 1 to 12 hours. Typically, the composition is applied in the morning and/or in the evening before bed. When used according to the methods herein, the present compositions can improve the appearance of hyperpigmented skin by inhibiting PAR2 activation, as demonstrated by an improvement in the size and/or color of the hyperpigmented spot. In some instances, the bilirubin reduction benefit provided by the water lily extract may be demonstrated by providing improved PAR2 activation inhibition relative to a predetermined value (i.e., determined prior to the beginning of the treatment period). Additionally or alternatively, the PAR2 activation inhibition benefit may be demonstrated in vitro by comparing the measured value of the inventive composition to a control value (e.g., vehicle control) or other reference value.

The treatment period for use of the compositions herein is ideally of sufficient time for the water lily extract and vitamin $B_3$ compound to improve the appearance of the hyperpigmentation condition. The treatment period may last for at least 1 week (e.g., about 2 weeks, 4 weeks, 8 weeks, or even 12 weeks). In some instances, the treatment period will extend over multiple months (i.e., 3-12 months). In some instances, the composition may be applied most days of the week (e.g., at least 4, 5 or 6 days a week), at least once a day or even twice a day during a treatment period of at least 2 weeks, 4 weeks, 8 weeks, or 12 weeks.

The step of applying the composition may be accomplished by localized application. In reference to application of the composition, the terms "localized", "local", or "locally" mean that the composition is delivered to the targeted area (e.g., a hyperpigmented spot or portion thereof) while minimizing delivery to skin surfaces where treatment is not desired. The composition may be applied and lightly massaged into an area of skin. The form of the composition or the dermatologically acceptable carrier should be selected to facilitate localized application. While certain embodiments herein contemplate applying a composition locally to an area, it will be appreciated that compositions herein can be applied more generally or broadly to one or more skin surfaces. In certain embodiments, the compositions herein may be used as part of a multi-step beauty regimen, wherein the present composition may be applied before and/or after one or more other compositions.

Methods

Phenolic Compound Assay.

This method provides a suitable means to determine the amount of polyphenolic compounds in the water lily extract. The polyphenolic compounds form, in the presence of potassium ferricyanide, colored compounds, detectable at 715 nm. The coloring intensity is proportional to the quantity of polyphenolic compounds. Readings are taken from a standard sample of gallic acid ranging between 40 and 120 mg/l. The results obtained for the samples allow a straight-line optical density to be traced as a function of the concentration and the polyphenols level of the samples is read directly on this straight line. The content of polyphenolic compounds of the hydrolysate according to the invention may be expressed as a percentage of gallic acid equivalent relative to the dry matter content of the water lily extract.

PAR2 Inhibition Assay

This method provides a suitable assay for measuring the ability of a material(s) to inhibit PAR2 activation. The assay principle relies on the recruitment of beta arrestin to the activated PAR2 receptor resulting in the formation of an active beta galactosidase enzyme, which cleaves a substrate producing a luminescent signal that can be quantitated. PAR2 can be activated by either adding trypsin and/or by adding SLIGRL.

Cells expressing PAR2 receptor coupled to the alpha fragment of beta galactosidase and expressing beta arrestin coupled to the beta fragment of beta galactosidase are obtained from DiscoveRx Corp., Freemont, CA. The cells are propagated in a culture medium of Dulbeccos Modified Eagle Medium supplemented with 10% heat-inactivated fetal bovine serum, 500 unit/mL penicillin, 500 ug/mL streptomycin, 800 ug/mL gentimicin, and 300 ug/mL hygromycin in T75 or T150 culture flasks (all media components available from Invitrogen Corp., Carlsbad, CA) in a $CO_2$ incubator at 37° C. When cells reach approximately 80% confluency, the cells are detached from the flask using Cell Dissociation Buffer (available from Invitrogen Corp., Carlsbad, CA). The cells are counted using a hemocytometer and plated into 384 well plates at 10000 cells/well in 20 uL/well of Opti-MEM® media (available from Invitrogen Corp., Carlsbad, CA). The cells are cultured for 24-48 hours.

To measure the ability of a material to inhibit PAR2 activation by trypsin, each well is treated with 1 uL of the test material in water. Each test material is run in triplicate. The cells are incubated for 30 minutes in the $CO_2$ incubator, after which 1 uL of trypsin is added (approximate 0.1 ug/uL). The cells are incubated for an hour in the $CO_2$ incubator after which the cell lysis substrate solution (11 uL/well) is added. The lysis substrate solution is available in the PathHunter™ Detection Kit (catalogue #93-0001) from DiscoveRx Corp., Freemont, CA, in which the components are mixed in the following ratio:

Assay Buffer:Substrate 1:Substrate 2=19:5:1

The plates are briefly centrifuged (approximately 5 minutes) at 800 times gravity (×g) to remove bubbles and are then incubated at room temperature for 1 hr. Luminescence is read for each well on an Envision™ 2101 brand multilabel reader (available form PerkinElmer, Inc., Boston, MA). The range is determined by wells with solvent control+trypsin (high control) and by wells with solvent control and no trypsin (low control). The percent PAR2 inhibition of each treatment is calculated by the following formula of the luminescence signals:

$$\left(1 - \frac{[\text{treatment luminescence} - \text{low control luminescence}]}{[\text{high control luminescence} - \text{low control luminescence}]}\right) \times 100$$

Statistics are done in Excel by using the T-test function, single tail with uneven distribution functions. P-values of $p \leq 0.1$ are considered statistically significant. P-values of $p \leq 0.25$ are considered trending.

EXAMPLES

Example 1: Formulations

Table 1 below provides examples of topical skin care compositions comprising water lily extract. The exemplary compositions are made by blending the A phase components with a suitable mixer (e.g., Tekmar RW20DZM or equivalent) and heating to a temperature of 70-80° C. and maintaining the temperature while stirring. Separately, the B phase components are blended with a suitable mixer and heated to 70-75° C., while maintaining temperature during mixing. Phase B is added to Phase A while mixing well to form an oil-in-water (O/W) emulsion. The emulsion is then milled using a suitable mill (e.g., Tekmar T-25 or equivalent) for 5 minutes. When the emulsion is at 60° C., phase C is added while continuing to mix. At 40° C., the ingredients of phase D and E are added to the emulsion. The emulsion is then milled for 5 minutes to provide a uniform composition.

TABLE 1

| Component | I | II | III | IV | V | VI | VII | VIII | IX |
|---|---|---|---|---|---|---|---|---|---|
| Phase A | | | | | | | | | |
| Water | qs | qs | qs | qs | qs | qs | qs | qs | qs |
| Glycerol | 5.00 | 7.00 | 3.00 | 15.0 | 7.00 | 5.00 | 5.00 | 3.00 | 5.00 |
| Disodium EDTA | 0.10 | 0.05 | 0.10 | 0.10 | 0.05 | 0.05 | 0.05 | 0.05 | 0.10 |
| Phase B | | | | | | | | | |
| Dimethicone 5 cSt | — | — | — | — | — | — | — | 10.0 | 15.0 |
| Dimethicone and Dimethicone Crosspolymer | — | — | — | — | — | — | — | 13.0 | 15.0 |
| Laureth-4 | — | — | — | — | — | — | — | 0.25 | 0.35 |
| Polysorbate 20 | — | — | — | — | — | — | — | 0.15 | 0.25 |
| Tapioca Starch and Polymethylsilsesquioxane | — | — | — | — | — | — | — | 2.50 | 3.50 |
| Avobenzone | — | — | — | 3.00 | — | 3.00 | — | — | — |
| Homosalate | — | — | — | 15.0 | — | 10.0 | — | — | — |
| Octisalate | — | — | — | 5.00 | — | 5.00 | — | — | — |

TABLE 1-continued

| Component | I | II | III | IV | V | VI | VII | VIII | IX |
|---|---|---|---|---|---|---|---|---|---|
| Octocrylene | — | — | — | 2.60 | — | 9.00 | — | — | — |
| Isopropyl Isostearate | 5.00 | 2.50 | 1.00 | — | — | — | — | — | — |
| Isohexadecane | 1.00 | 1.50 | 3.00 | — | — | — | — | — | — |
| Cetyl Alcohol | 0.25 | 0.50 | 0.32 | 0.40 | 0.40 | 0.30 | 0.50 | — | — |
| Tocopherol Acetate | | 0.50 | 0.25 | 1.00 | 0.25 | 0.25 | 0.25 | — | — |
| PEG-100 Stearate | 0.20 | 0.10 | 0.10 | 0.30 | 0.10 | 0.20 | 0.10 | — | — |
| Stearyl Alcohol | 0.50 | 1.50 | 0.40 | 0.60 | 0.50 | 0.40 | 0.60 | — | — |
| Behenyl Alcohol | 0.40 | 1.00 | 0.50 | 0.50 | 0.40 | 0.35 | 0.50 | — | — |
| Ethyl Paraben | 0.20 | 0.15 | 0.20 | 0.25 | — | — | — | — | — |
| Propyl Paraben | 0.10 | 0.15 | 0.10 | 0.15 | — | — | — | — | — |
| Polymethylsilsesquioxane | 1.25 | 2.50 | 1.00 | — | — | — | — | — | — |
| Phase C | | | | | | | | | |
| Titanium Dioxide | — | 0.50 | — | 0.25 | — | — | — | — | — |
| Tapioca Starch and Polymethylsilsesquioxane | — | — | — | — | — | 12.0 | — | — | — |
| Vinyl Dimethicone/Methicone Silsesquioxane Crosspolymer | 1.50 | | 1.50 | 3.50 | 5.00 | — | 7.50 | — | — |
| Sodium Polyacrylate Starch | — | — | — | — | 1.50 | 1.00 | 1.50 | — | — |
| Hydroxyethyl acrylate/sodium acryloyldimethyltaurate copolymer | 2.00 | 1.50 | 2.50 | 2.00 | — | — | — | 1.25 | 2.00 |
| Phase D | | | | | | | | | |
| Water | 5.00 | 10.0 | 10.0 | 5.00 | 10.0 | 10.0 | 10.0 | 5.00 | 10.0 |
| Water Lily Extract | 0.05 | 0.40 | 1.00 | 0.40 | 0.40 | 0.20 | 1.00 | 1.00 | 0.25 |
| Niacinamide | 2.00 | | 3.50 | | 4.00 | 5.00 | — | | 2.00 |
| Dexpanthenol | 0.25 | 0.50 | 0.50 | 1.00 | 1.00 | 1.50 | 0.25 | 1.00 | 0.50 |
| Phase E | | | | | | | | | |
| Benzyl alcohol | 0.25 | 0.40 | 0.25 | 0.50 | — | — | — | — | — |
| Hexanediol and Caprylyl Glycol | — | — | — | — | 0.70 | 0.80 | 0.70 | 0.70 | 1.00 |
| Phenoxyethanol | — | — | — | — | 0.3 | 0.4 | 0.5 | 0.20 | 0.25 |
| Dimethicone/dimethiconol | 0.5 | 1.00 | 2.00 | 1.00 | 2.00 | 2.00 | 1.00 | 1.75 | 1.00 |

Example 2: Liquid Water Lily Extract

This example describes a process for providing a suitable water lily extract for use in the cosmetic compositions herein. In this example, flowers of the *Nymphaea alba* plant are dried and then ground into a powder. The dried powder is solubilized in water (100 g/L) and subjected to enzymatic hydrolysis with a carbohydrase (e.g., cellulase, glucanase, pectinase, xylanase, arabinose or a combination of these) and a protease (e.g., endoprotease, cysteinprotease, exopeptidase, aminopeptidase, metalloprotease or a combination of these). The soluble (i.e., aqueous) and insoluble phases are separated and the insoluble phase can be discarded. The soluble phase is thermally treated to inactivate any enzymes that may be present. The solution is then clarified and purified. The concentration of the clarified and purified solution can be adjusted to the desired level by adding or removing water. The solution is then filtered and sterilized to provide the water lily extract for incorporation into a product. Table 3 below lists a non-limiting examples of physical characteristics of the resulting water lily extract. The amounts of polyphenol, carbohydrate, protein and mineral shown in in Table 2 are all weight percentages based on the weight of the dry matter.

TABLE 3

| Property | Value |
|---|---|
| Dry Matter content | 29 g/L |
| Polyphenol content | <0.2% (threshold detection) |
| Carbohydrate content | 51% |
| Protein content | 10% |
| Mineral content | 39% |

Example 3: Synergistic Inhibition of PAR2 Activation

This example demonstrates the ability of an effective amount of a combination of water lily extract and vitamin $B_3$ compound to synergistically inhibit PAR2 activation. The water lily extract in this test is *Nymphaea alba* flower extract obtained from Silab, France. The water lily extract used in this test is not commercially available. The vitamin $B_3$ compound is niacinamide obtained from Sigma Aldrich, St. Louis, MO as product #N5535. The water lily extract and niacinamide were tested at ratios ranging from 1:100 to 20:1 (water lily:niacinamide). The ability of the combinations of water lily extract and niacinamide to inhibit PAR2 activation were determined according to the PAR2 Inhibition Assay above. Synergy Factor is calculated as:

$$\frac{\text{observed inhibition of } B3 + \text{water lily}}{\text{inhibition of } B3 \text{ alone} + \text{inhibition of water lily alone}}$$

A synergy factor greater than 1.00 with p-value≤0.05 indicates statistically significant synergy. The results of the test are summarized in Table 3 below.

TABLE 3

| WL:N | Observed Inhibition | Expected Inhibition | Synergy Factor | p-value observed vs. expected |
|---|---|---|---|---|
| 1:100 | 23 | 24 | 0.96 | 0.87 |
| 1:4 | 29 | 27 | 1.07 | 0.78 |
| 1:2 | 65 | 29 | 2.24 | 0.0007 |
| 1:1 | 74 | 33 | 2.24 | 0.003 |
| 2.5:1 | 63 | 34 | 1.85 | 0.012 |

TABLE 3-continued

| WL:N | Observed Inhibition | Expected Inhibition | Synergy Factor | p-value observed vs. expected |
|---|---|---|---|---|
| 5:1 | 39 | 32 | 1.22 | 0.11 |
| 20:1 | 28 | 32 | 0.88 | 0.23 |

As can be seen in Table 3, only ratios of water lily extract to niacinamide of 1:4 to 5:1 demonstrated inhibition of PAR2 activation. Whereas ratios outside of these did not provide synergistic PAR2 activation inhibition.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical skin care composition, comprising:
    a. a hydrolysate comprising an aqueous extract of *Nymphaea alba* flowers and thermally inactivated enzymes; wherein the hydrolysate comprises from about 20% to about 70% carbohydrate, by weight of the dry matter of the hydrolysate;
    b. a vitamin $B_3$ compound; and
    c. a dermatologically acceptable carrier.

2. The skin care composition of claim 1, wherein the vitamin $B_3$ compound is niacinamide and is present at about 0.001% to about 10%, by weight of the composition.

3. The skin care composition of claim 1, wherein the composition comprises about 0.0001% to about 10%, by weight of the composition, of the hydrolysate.

4. The skin care composition of claim 1, wherein the hydrolysate comprises about 20% to about 60% mineral based on the weight of the dry matter of the hydrolysate.

5. The skin care composition of claim 1, wherein the hydrolysate comprises less than about 3% polyphenol based on the weight of the dry matter of the hydrolysate.

6. The skin care composition of claim 1, wherein the composition further comprises at least one additional ingredient chosen from vitamins, minerals, sugar amines, sunscreen agents, oil control agents, flavonoid compounds, anti-oxidants, preservatives, protease inhibitors, tyrosinase inhibitors, anti-inflammatory agents, moisturizing agents, exfoliating agents, skin lightening agents, lubricants, anti-acne actives, chelating agents, anti-wrinkle actives, anti-atrophy actives, phytosterols, N-acyl amino acid compounds, antimicrobials, and antifungals, conditioning agents, emulsifiers, rheology modifiers, or mixtures thereof.

7. The skin care composition of claim 6, wherein the additional ingredient is chosen from superabsorbent polymer thickening agent selected from sodium polyacrylate, starch grafted sodium polyacrylate, or mixtures thereof.

8. The skin care composition of claim 1, wherein the hydrolysate comprises less than 15% peptide, based on the weight of dry matter of the hydrolysate.

9. The skin care composition of claim 1, wherein the hydrolysate comprises less than 10% peptide, based on the weight of dry matter of the hydrolysate.

10. The skin care composition of claim 1, wherein the hydrolysate and vitamin $B_3$ compound are present at a volume/weight ratio of hydrolysate to vitamin $B_3$ of 1:4 to 5:1.

11. The skin care composition of claim 1, wherein the hydrolysate and vitamin $B_3$ compound are present at a volume/weight ratio of hydrolysate to vitamin $B_3$ compound of 1:2 to 2.5:1.

12. The skin care composition of claim 1, wherein the vitamin $B_3$ compound is niacinamide.

13. The skin care composition of claim 1, wherein the vitamin $B_3$ is present at about 0.0001% to about 10%, by weight of the composition.

* * * * *